US012642982B2

(12) United States Patent
Vaidyanathan

(10) Patent No.: US 12,642,982 B2
(45) Date of Patent: Jun. 2, 2026

(54) ELECTRICAL OPTICAL MEDICAL LEAD

(71) Applicant: Medtronic, Inc., Minneapolis, MN (US)

(72) Inventor: Janardan Vaidyanathan, Thane (IN)

(73) Assignee: Medtronic, Inc., Minneapolis, MN (US)

( * ) Notice: Subject to any disclaimer, the term of this patent is extended or adjusted under 35 U.S.C. 154(b) by 679 days.

(21) Appl. No.: 17/933,710

(22) Filed: Sep. 20, 2022

(65) Prior Publication Data

US 2023/0096373 A1      Mar. 30, 2023

Related U.S. Application Data

(60) Provisional application No. 63/246,106, filed on Sep. 20, 2021.

(51) Int. Cl.
A61N 5/01          (2006.01)
A61N 5/06          (2006.01)
(52) U.S. Cl.
CPC .............. A61N 5/01 (2013.01); A61N 5/0601 (2013.01); A61N 5/0622 (2013.01); A61N 2005/063 (2013.01); A61N 2005/0651 (2013.01)
(58) Field of Classification Search
CPC ...... A61N 5/01; A61N 5/0601; A61N 5/0622; A61N 2005/063; A61N 2005/0651; A61N 2005/0612
See application file for complete search history.

(56) References Cited

U.S. PATENT DOCUMENTS

| | | | | |
|---|---|---|---|---|
| 5,334,207 A | * | 8/1994 | Gay, Jr. ................ | A61B 18/245 |
| | | | | 606/7 |
| 7,883,536 B1 | | 2/2011 | Bendett et al. | |
| 8,498,699 B2 | | 7/2013 | Wells et al. | |
| 8,632,577 B1 | | 1/2014 | Bendett et al. | |
| 8,864,806 B2 | | 10/2014 | Wells et al. | |
| 10,046,174 B2 | | 8/2018 | Deisseroth et al. | |
| 10,702,697 B2 | * | 7/2020 | Chabrol ............... | A61N 5/0601 |
| 10,716,942 B2 | | 7/2020 | Zhang | |
| 2005/0247472 A1 | | 11/2005 | Helfer et al. | |
| 2011/0125077 A1 | | 5/2011 | Denison et al. | |
| 2011/0125078 A1 | | 5/2011 | Denison et al. | |
| 2012/0253261 A1 | | 10/2012 | Poletto et al. | |
| 2012/0290025 A1 | | 11/2012 | Keimel | |
| 2013/0317573 A1 | * | 11/2013 | Zhu ..................... | A61N 1/0551 |
| | | | | 607/89 |
| 2015/0306414 A1 | | 10/2015 | Nielsen et al. | |
| 2015/0306415 A1 | | 10/2015 | Tischendorf et al. | |
| 2015/0375006 A1 | | 12/2015 | Denison et al. | |
| 2019/0201709 A1 | | 7/2019 | Tischendorf et al. | |
| 2021/0059779 A1 | | 3/2021 | Zhao et al. | |
| 2025/0090860 A1 | * | 3/2025 | Tsukamoto ............ | A61N 5/062 |

* cited by examiner

*Primary Examiner* — John R Downey

(74) *Attorney, Agent, or Firm* — Shumaker & Sieffert, P.A.

(57) ABSTRACT
An implantable medical system includes a light delivery module comprising a light source that generates light and a controller that controls the output of the light source, a lead with a plurality of electrodes, the lead extending from a proximal end to a distal end, wherein the lead further comprises an optical light guide configured to deliver the light from the light source, and the controller is configured to deliver voltage across two or more of the electrodes to steer a distal end of the optical light guide, to provide electrical stimulation or sense/record electrical signals.

21 Claims, 7 Drawing Sheets

700  CONTROL DELIVERY OF VOLTAGE ACROSS ELECTRODES OF A LEAD

702  STEERING A DISTAL END OF AN OPTICAL LIGHT GUIDE OF AN IMPLANTABLE LEAD

704  DELIVER LIGHT TO A TARGET TISSUE VIA THE OPTICAL LIGHT GUIDE

706  DELIVER ELECTRICAL STIMULATION TO TISSUE VIA ELECTRODES OF THE IMPLANTABLE LEAD

ELECTRICAL OPTICAL MEDICAL LEAD

This application claims the benefit of U.S. Provisional Patent Application No. 63/246,106, filed 20 Sep. 2021, the entire contents of which is incorporated herein by reference.

TECHNICAL FIELD

The disclosure relates to a device and system for an electrical optical medical lead.

BACKGROUND

Electrical stimulation of neural tissue serves as the core of many neurological therapies, and can provide relief for a variety of disorders, improving the quality of life for many patients. In some cases, electrical stimulation may be characterized by a lack of specificity in the excitation of neural tissue. In particular, it can be difficult to stimulate a specific, localized neural population due to constraints on electrode geometry and placement. For example, the area of stimulation may be dictated by electrode size, which can be generally orders of magnitude greater than the cellular targets of interest. In some cases, this may lead to overexciting cellular networks and/or inefficient stimulation, and may result in stimulation of non-target cells. In addition, inhibitory stimuli through the use of electrical coupling generally may be accomplished only through an electrical stimulation block that involves inefficient, high frequency stimulation, thereby limiting the therapy modulation strategy in some circumstances. In addition, electrical stimulation can undermine the ability to sense underlying electrical neural activity simultaneously with delivery of electrical stimulation. In particular, electrical stimulation currents flowing through the tissue that are necessary to achieve a localized current density high enough to depolarize the cell or axon can mask the bioelectrical activity to be sensed (e.g., a stimulus artifact).

SUMMARY

In general, the disclosure describes techniques for an implantable medical system having an optical device with an electrical lead, and steering the optical device relative to the electrical lead of the medical system to direct light to target tissue. The electrical lead may include two or more electrodes that may create a magnetic field to steer the optical device in one or more different directions.

In some examples, an implantable medical system includes a light delivery module comprising a light source that generates light and a controller that controls the output of the light source, a lead with a plurality of electrodes, the lead extending from a proximal end to a distal end, wherein the lead further comprises an optical light guide configured to deliver the light from the light source, and the controller is configured to deliver voltage across two or more of the electrodes to steer a distal end of the optical light guide.

In some examples, a system includes a memory, processing circuitry configured to control delivery of voltage across electrodes of a lead to steer a distal end of an optical light guide of the lead, and control a light source to transmit light to a patient via the optical light guide of the lead.

In some examples, a method includes controlling delivery of voltage across electrodes of a lead to steer a distal end of an optical light guide of the lead, and transmitting light from a light source of an implantable medical system to a patient via the optical light guide of the lead.

In some examples, an implantable medical system includes a lead with a plurality of electrodes along a lead body, a substrate within the lead, the substrate having two or more light sources, wherein the substrate includes metallic material, and a controller configured to deliver voltage across two or more of the electrodes to steer portions of the substrate within the lead body.

The details of one or more examples of the invention are set forth in the accompanying drawings and the description below. Other features, objects, and advantages of the invention will be apparent from the description and drawings, and from the claims.

DETAILED DESCRIPTION

Figure 1:
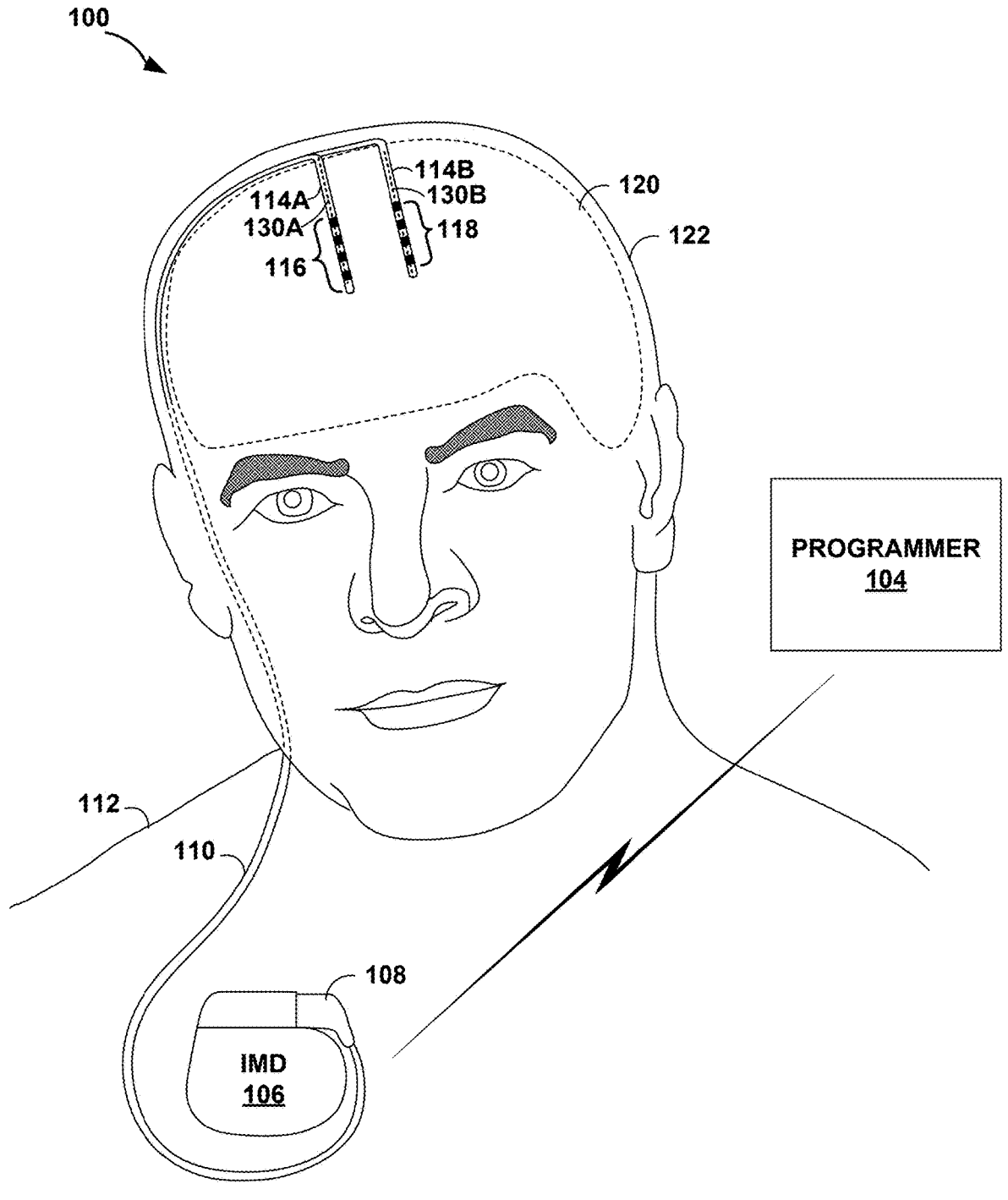
FIG. 1 is a conceptual diagram illustrating an example implantable medical system that includes an implantable stimulator coupled to one or more optical light guides and one or more electrodes.

This disclosure describes various devices, systems, and techniques including an implantable medical system for steering an optical light guide of an electrical-optical lead with electrical voltage. In some examples, the optical light guide may be positioned to deliver optical stimulation to target neural tissue using the steering techniques. In some non-limiting examples, the lead may also provide electrical and/or optical stimulation. In some examples, optical stimulation may be provided, and sensors may sense/record local field potentials (LFP). Some advantages of optical stimulation may include a lack of electrical artifact in sensed signals which normally occurs with electrical stimulation. In some examples, electrical stimulation may lack specificity and selectivity when applied to neural tissue in selecting the individual neural component or substrate at target. Optical stimulation may have a higher spatial resolution in comparison to electrical stimulation.

In some examples, stimulation may be delivered to target tissue within the brain or spinal cord of a human patient. However, the disclosure is not so limited. Rather, stimulation may be delivered to any of a variety of target tissue sites to support any of a variety or therapies. A few examples include without limitation cardiac tissue to support cardiac therapy such as pacing, cardioversion, defibrillation, resynchronization, or other therapies, gastrointestinal tissue to support gastrointestinal therapy such as therapy to address obesity, eating disorders, motility disorders (e.g., gastroparesis), dyspepsia, or other therapies, pelvic floor tissue (e.g., sacral or pudendal nerve tissue) to support pelvic floor therapy such as pain therapy, urinary or fecal incontinence therapy, sexual dysfunction, or other therapies, or cranial tissue to support cranial nerve therapy such as therapy to relieve occipital neuralgia, trigeminal neuralgia, facial pain, migraine headaches, or neural tissue to support neural therapy such as movement disorders, epilepsy, memory disorders, psychiatric disorders or auditory system or the like.

The implantable medical system may be fully implantable in the patient. In other examples, some portions of the implantable medical system may be implantable in the patient, while other components are configured to be external to the patient. For example, one or more programmers may be external to the patient, and communicate with an implanted device via wireless telemetry. In other cases, a stimulation generator may be external to the body, and be configured to deliver light via percutaneously implanted optical delivery elements (such as optical light guides), leads and/or conduits. Optical light guides will be described for purposes of illustration, but without limitation as the use of other types of optical delivery elements, including single or multi strand fiber optic cable or single-fiber optical light guide, or multi-fiber optical light guide. In some examples, optical therapy may be delivered via a tip or side of the optical light guide.

FIG. 1 is a conceptual diagram illustrating an example system 100 that includes an implantable medical device (IMD) 106 configured to deliver deep brain stimulation (DBS) to patient 112 according to an example of the techniques of the disclosure. As shown in the example of FIG. 1, example system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. One or more implantable optical light guides 130A, 130B may be disposed within one or both leads 114A, 114B, respectively. In some examples, optical light guides 130A, 130B may extend along substantially the entire length of the lead, for connection to the light source. In some examples, optical light guides 130A, 130B may be centered or offset within a lumen in the lead body. In some examples, there is no lead extension for lead 114 such that waveguide extends all the way back to the connector in the IMD. In some examples, the lead 114 may include a lead extension with an optical coupler to receive the waveguide and interface it with another waveguide within the lead extension for optical communication from the light source to the waveguide. For example, there may be two or more waveguides connected in series.

IMD 106 may also deliver optical stimulation, such as light, to patient 112 via the one or more implantable optical light guides 130A, 130B within leads 114A and 114B. The terms "light" or "optical light" as used herein refer, for example, to electromagnetic radiation having a wavelength and intensity that has a physiologically measurable effect and may include visible light, infrared light, and ultraviolet light. In some examples, light that may be used to provide the optical stimulation of system 100 may include visible light having a wavelength of between about 380 nm and about 750 nm, infrared light having a wavelength of between about 700 nm and about 300 μm, and ultraviolet light having a wavelength between about 10 nm and about 400 nm. In some examples, a first optical light guide 130A may deliver visible light having a certain wavelength and intensity, and a second optical light guide 130B may deliver visible light having the same wavelength and intensity, or a different wavelength at the same intensity, or the same wavelength and a different intensity, or the second optical light guide 130B may deliver non-visible light, such as infrared or ultraviolet light. The optical light guides 130A and 130B may be coupled to the same light source or different light sources. In some cases, a single light source may be optically multiplexed across the light guides 130A, 130B to deliver light via the different guides at different times. In some examples, the light source may deliver light via both light guides 130A, 130B simultaneously. The light delivered via one optical light guide 130A may be the same as the light delivered via another optical light guide 130B, e.g., in terms of characteristics or parameters such as wavelength, amplitude, pulse width or pulse rate. Alternatively, the light delivered via the optical light guides 130A, 130B may have different characteristics or parameters. In some examples, two or more different sources of light may be able to provide two different wavelengths, which may allow for optical stimulation to reach different depths of tissue.

The implantable optical light guides 130A, 130B may be deployed to a target site as part of one or more bundles of optical light guides, within leads 114A, 114B. In some cases, optical light guides 130A, 130B may be steered within leads 114A, 114B to precisely position the optical light guides with respect to target tissue sites. The optical stimulation may be in the form of optical light of a particular wavelength and may be delivered as pulses, e.g., with a defined pulse width and pulse rate. Various parameters of the pulses may be defined by a stimulation program. The pulses may be delivered substantially continuously for a relatively long period of time, such as several seconds or more, or in pulse bursts, segments, or patterns, and may be delivered alone or in combination with pulses defined by one or more other stimulation programs (cycling and/or interleaving).

In some examples, IMD 106 may generate programmable optical stimulation, e.g., optical pulses with selected wavelengths and intensities, and delivers the stimulation via one or more implantable optical light guides 130. In some cases, the wavelengths and intensities of the optical pulses may be fixed, or limited to a narrow range. In other examples, the wavelengths and intensities of the optical pulses may be variable, i.e., tunable to produce a wider range of desired wavelengths and intensities. In some cases, multiple sets of one or more implantable optical light guide 130 may be provided. In the example of FIG. 1, two optical light guides 130A and 130B (collectively referred to as "optical light guide 130") may be each carried as part of an optical fiber bundle until a distal end of bundle is bifurcated into separate optical light guides 130. Each optical light guide 130A, 130B may be a single optical fiber. Alternatively, in some examples, each optical light guide may include multiple light guides that together deliver optical stimulation. IMD 106 may provide optical stimulation by generating optical light with a desired wavelength and intensity, and directing the optical light with the optical light guide 130.

Other means of light communication may be used in place of an optical light guide, including an optical fiber, wave guide, a hollow tube, a liquid filled tube, a substrate including a light guide, and a light pipe. In another example, a light source, such as a light emitting diode (LED), is implanted at the target treatment site, e.g., at the distal end of a substrate of a lead, such that the light is emitted into the target tissue from the LED, rather than via an optical fiber. In this case, a conducting lead may be implanted to extend from an optical stimulation controller to the LED to conduct electrical energy to power the light source. In some examples, a light source or sources may include quantum dots (QDs).

In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120, e.g., on a selective basis.

IMD 106 includes a therapy module (e.g., which may include processing circuitry, optical signal generation circuitry, electrical stimulation circuitry or other circuitry configured to perform the functions attributed to IMD 106) that includes a stimulation generator configured to generate and deliver electrical voltage across a subset of electrodes 116, 118 of leads 114A and 114B, respectively to steer a distal end of the optical light guides 130A, 130B. The stimulation generator also may be configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination/configuration. The group of electrodes 116, 118 includes at least one electrode and can include a plurality of electrodes. In some examples, the plurality of electrodes 116 and/or 118 may have a complex electrode geometry such that two or more electrodes of the lead are located at different positions around the perimeter of the respective lead (e.g., different positions around a longitudinal axis of the lead). In some examples, at least one electrode includes at least two electrodes disposed at different axial positions along the lead in the patient. In some examples, at least one electrode includes at least two electrodes disposed at different axial positions along the lead, and may be disposed at a same circumferential position around a perimeter of the lead. Various designs in low and high resolution with or without an active tip (passive tip) are contemplated.

In some examples, neurological signals (e.g., an example type of electrical signals) sensed within brain 120 may reflect changes in electrical current produced by the sum of electrical potential differences across brain tissue. Examples of neurological brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112.

Electrical stimulation and/or optical stimulation generated by IMD 106 may be configured to manage a variety of disorders and conditions. In some examples, the stimulation generator of IMD 106 may be configured to generate and deliver electrical and/or optical stimulation pulses to patient 112 via electrodes of a selected stimulation electrode combination and/or optical light guides 130A, 130B. However, in other examples, the stimulation generator of IMD 106 may be configured to generate and deliver a continuous wave signal, e.g., a sine wave or triangle wave or any other charge balanced waveform. In either case, a stimulation generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, waveform pattern, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. IMD 106 may deliver electrical stimulation intended to contribute to a therapeutic effect. In some examples, IMD 106 may also, or alternatively, deliver electrical stimulation intended to be sensed by other electrodes and/or elicit a physiological response, such as an evoked compound action potential (ECAP) or resonant response, that can be sensed by electrodes. IMD 106 may deliver optical stimulation intended to contribute to a therapeutic effect. In some examples, IMD 106 may also, or alternatively, deliver optical stimulation intended to be sensed by other electrode and/or elicit a physiological response. In some examples IMD 106 may deliver sub-threshold electrical stimulation to an electrode combination/configuration in order to steer optical stimulation in the intended anatomical direction within target tissue/region.

IMD 106 may be implanted within a subcutaneous pocket below the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical and/or optical stimulation to and/or record/sense from one or more regions of brain 120, which may be selected based on the patient condition or disorder controlled by therapy system 100. The specific target tissue site and the stimulation electrodes used to deliver stimulation to the target tissue site, however, may be selected, e.g., according to identified patient behaviors, e.g., as patient behaviors associated with one or more brain disorders and/or other sensed patient signals. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead implanted in a single hemisphere. Although leads 114 may have ring/omnidirectional electrodes at different longitudinal positions as shown in FIG. 1, leads 114 may have electrodes disposed at different positions around the perimeter of the lead to directionally fractionalize delivered stimulation as in a segmented/windowed lead (e.g., different circumferential positions for a cylindrical shaped lead) as shown in the examples of FIGS. 3, 4, 5A, 5B, and 6. Leads 114 could be of active (or bullet) or passive tip design.

Leads 114 illustrate an example lead set that includes axial leads carrying ring electrodes disposed at different axial positions (or longitudinal positions along the lead shaft). In some examples, leads 114 may have segmented electrodes, e.g., with some electrodes at different axial and circumferential/radial positions. In other examples, leads may be referred to as "paddle" leads carrying planar arrays of electrodes on one side of the lead structure. In addition, as described herein, complex lead array geometries may be used in which electrodes are disposed at different respective longitudinal (i.e., axial) positions and different positions around the perimeter of the lead. As described herein, IMD 106 may be configured to detect movement of the lead with respect to tissue when monitoring electrical signals sensed by the different electrodes between different times.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical and/or optical stimulation to one or more target tissue sites within brain 120 to manage patient symptoms associated with a movement disorder, or neurological or psychiatric disorders of patient 112 in addition to being able to sense/record patient signals. Leads 114 may be implanted to position electrodes 116, 118 at desired locations of brain 120 through respective burr holes in cranium 122. Leads 114 may be placed at any location within brain 120 such that electrodes 116, 118 are capable of providing electrical and/or optical stimulation to target tissue sites within brain 120 during treatment or sense/record brain signals. For example, electrodes 116, 118 may be surgically implanted under the dura mater of brain 120 or within the cerebral cortex of brain 120 via a burr hole in cranium 122 of patient 112, and electrically and/or optically coupled to IMD 106 via one or more leads 114.

In the example shown in FIG. 1, electrodes 116, 118 of leads 114 are shown as ring (or omnidirectional) electrodes. Ring electrodes may be used in DBS applications because they are relatively simple to program and are capable of delivering an electrical field to any tissue adjacent to electrodes 116, 118. In other examples, electrodes 116, 118 may have different configurations. For example, in some examples, at least some of the electrodes 116, 118 of leads 114 may have a complex electrode array geometry (with an active or passive tip) that is capable of producing shaped electrical fields. The complex electrode array geometry may include multiple electrodes (e.g., partial ring or segmented electrodes) around the outer perimeter of each lead 114, rather than one ring electrode, such as the examples shown in FIGS. 3, 4, 5A and 5B. In this manner, electrodes 116, 118 may be used to create different magnetic and/or electric fields in multiple different positions or sense/record from pre-configured directions. In some examples, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient signals and the identified patient behaviors (e.g., brain state, symptom state or disease state). IMD 106 may generate electrical stimulation based on the selected therapy program to manage the patient symptoms associated with a movement disorder, or neurological or psychiatric disorders.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs, capture tagged/untagged events for sensing and/or view and modify therapy parameters. The clinician programmer may include more programming features than the patient programmer. In other words, more complex or sensitive tasks may only be allowed by the clinician programmer to prevent an untrained patient from making undesirable changes to IMD 106. IMD 106 may also transmit notifications to programmer 104 for delivery to a user in response to detecting that one of leads 114 has moved with respect to tissue. Programmer 104 may enter a new programming session for the user to select new stimulation parameters for subsequent therapy.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration (and orientation if applicable) of electrode array 116, 118, initial programs defining therapy parameter values, sensing and/or stimulation overview, information regarding steering optical light guides 130A, 130B via electrodes 116, 118, and any other information the clinician desires to program into IMD 106. Programmer 104 may also be capable of completing functional tests (e.g., measuring the impedance of electrodes 116, 118 of leads 114). In some examples, programmer 104 may receive sensed signals or representative information and perform the same techniques and functions attributed to IMD 106 herein. In other examples, a remote server (e.g., a standalone server or part of a cloud service) may perform or control some of the functions attributed to IMD 106, programmer 104, or any other devices described herein.

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combination with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.) and/or sensed/recorded patient signals. Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters, set an available range of values for a particular therapy parameter or trigger capturing events through sensing with tags (e.g., took medications).

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, or generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator or external neurostimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112 in other examples. In other examples, system 100 may include an implantable drug pump in addition to, or in place of, IMD 106. Further, an IMD may provide other electrical stimulation such as spinal cord stimulation to treat a movement disorder.

System 100 (e.g., IMD 106) may also include processing circuitry configured to control delivery of electric signals to electrode combinations to create a magnetic field. In some examples, optical light guide 130 may include material, such as metallic material, that may be affected or otherwise influenced by a magnetic field. In some examples, processing circuitry may control delivery of subthreshold electric signals (e.g., signals with parameters such as amplitude, pulse width, frequency, waveform pattern or a combination thereof) below an electrical stimulation activation threshold of patient 112 to electrodes in order to steer a distal end of the optical light guide 130. In some examples, processing circuitry may control delivery of electric signals to electrodes in order to steer a distal end of the optical light guide 130 to provide therapy to target tissue, e.g., by directing light emitted by the optical light guide 130 at the target tissue site. In some examples, the optical light guide 130 may be selectively steered to emit light toward a plurality of different target tissue sites, e.g., at different times.

The architecture of system 100 illustrated in FIG. 1 is shown as an example. The techniques as set forth in this disclosure may be implemented in the example system 100 of FIG. 1, as well as other types of systems not described specifically herein. Nothing in this disclosure should be construed so as to limit the techniques of this disclosure to the example architecture illustrated by FIG. 1.

Figure 2:
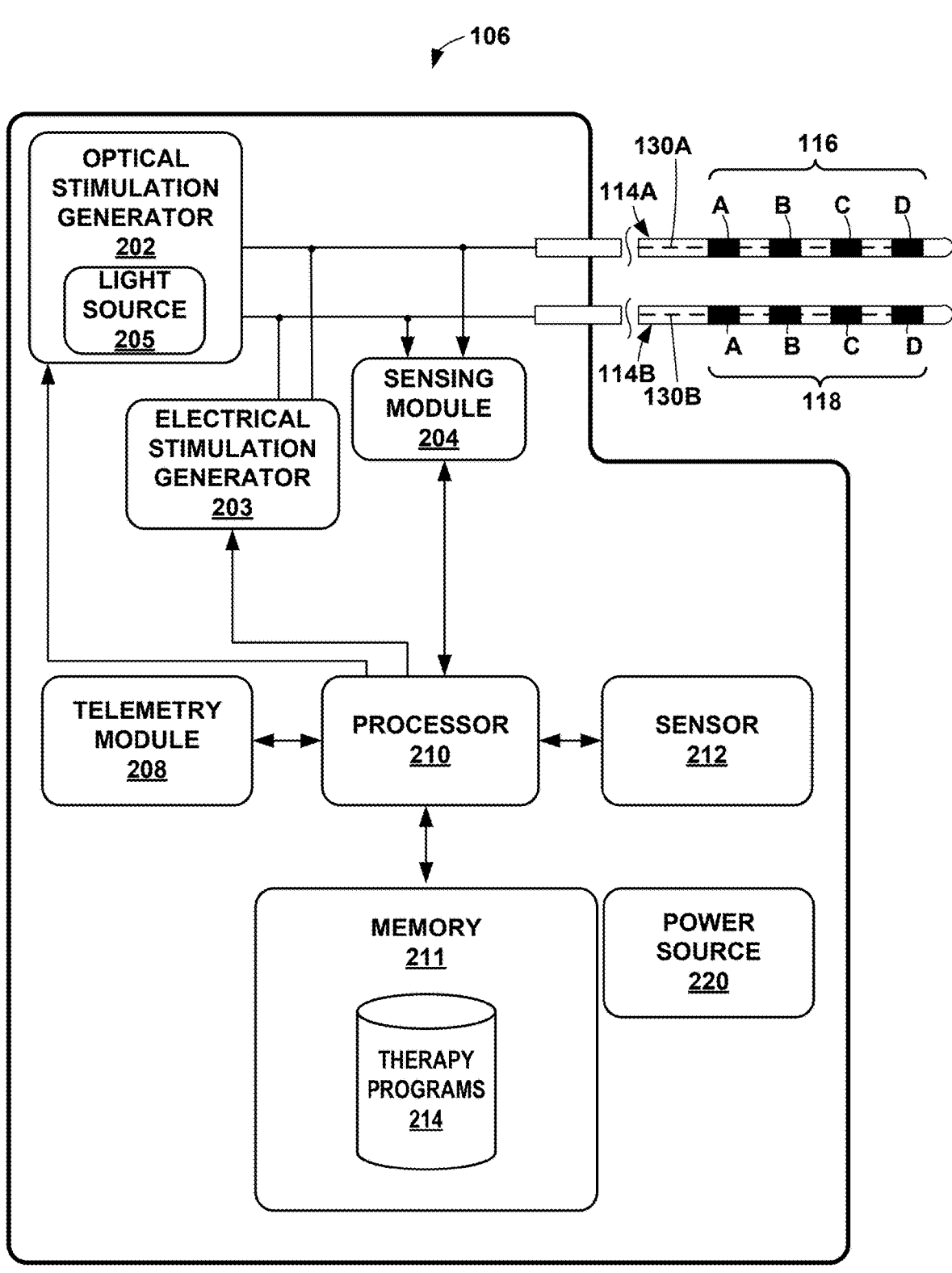
FIG. 2 is a block diagram illustrating various example components of an implantable medical system.
Figure 3:
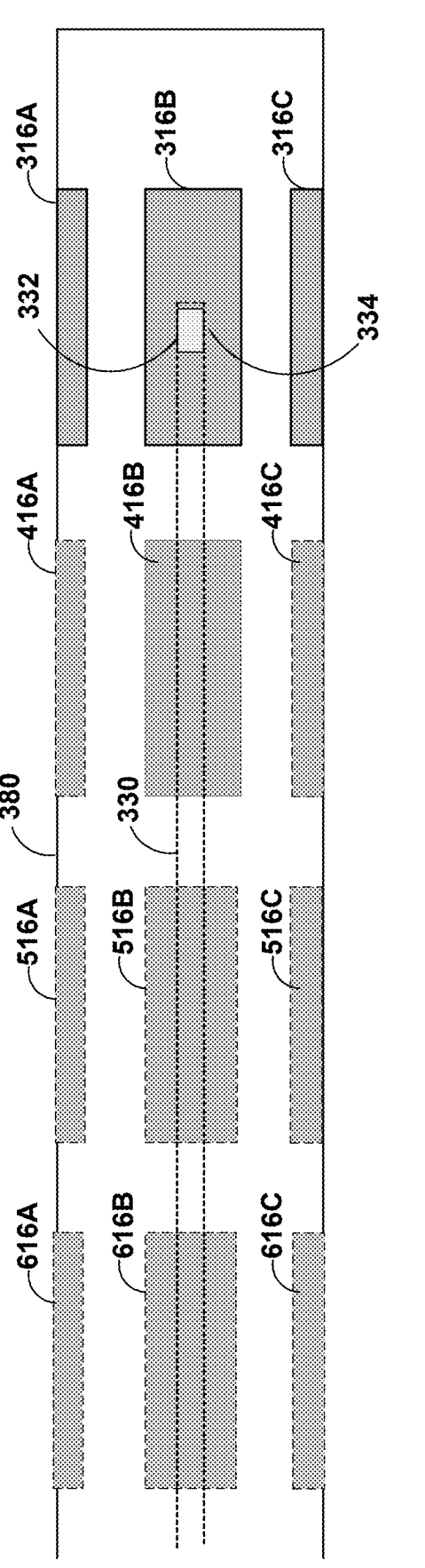
FIG. 3 is a conceptual diagram illustrating a side view of a lead of the implantable medical system in accordance with aspects of this disclosure.

FIG. 2 is a block diagram of the example IMD 106 of FIG. 1 for delivering DBS therapy. In the example shown in FIG. 2, IMD 106 includes processor 210, memory 211, optical stimulation generator 202 with light source 205, electrical stimulation generator 203, sensing module 204, telemetry module 208, sensor 212, and power source 220. Each of these modules may be or include electrical circuitry configured to perform the functions attributed to each respective module. For example, processor 210 may include processing circuitry, sensing module 204 may include sensing circuitry, and telemetry module 208 may include telemetry circuitry. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 106 to perform various functions. Memory 211 may be a storage device or other non-transitory medium.

In some examples, IMD 106 may deliver both optical stimulation therapy and electrical stimulation therapy, e.g., on a selective, alternating or substantially simultaneous basis. In other examples, IMD 106 may deliver only optical stimulation therapy and not deliver electrical stimulation therapy. In either cases, IMD 106 may electrically sense neural signals, e.g., to control or adjust optical stimulation therapy and/or electrical stimulation therapy. In the example shown in FIG. 2, memory 211 may store therapy programs that include respective stimulation parameter sets that define therapy. Each stored therapy program may define a particular set of electrical or optical stimulation parameters (e.g., a therapy parameter set), such as a waveform pattern, stimulation electrode combination, electrode polarity, current or voltage amplitude, intensity, pulse width, pulse rate and wavelength. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

In some examples, the sense and stimulation electrode combinations may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination and vice versa. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate irregular oscillations or other irregular brain activity within the tissue site associated with the sense electrode combination. In other examples, the electrodes that deliver stimulation may be carried by a lead implanted in a different region of the brain than a different lead that carries the sensing electrodes. As further shown in FIG. 2, each lead 114 may include an optical light guide 130. In some examples, optical stimulation is provided by the optical light guide 130.

Processor 210 may control optical stimulation generator 202 to deliver optical signals, e.g., as stimulation pulses, with intensities, wavelengths, pulse widths (if applicable), and rates specified by one or more stimulation programs. Processor 210 may also control optical stimulation generator 202 to selectively deliver the stimulation via subsets of optical light guides 130, which may be directed to different target tissue sites.

Upon selection of a particular program group, processor 210 may control optical stimulation generator 202 to deliver optical stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. In addition, each program may specify a particular optical fiber combination for delivery of optical stimulation. The optical fiber combination may specify particular optical fibers in a single array or multiple arrays.

Optical stimulation generator 202, which may also be known as a light delivery module, is coupled to optical light guides 130, and the optical light guides 130 are optically coupled with light source 205. Optical stimulation generator 202 may include stimulation generation circuitry to control light source 205 to generate stimulation pulses and circuitry for switching stimulation across different optical light guide combinations, e.g., in response to control by processor 210. Optical stimulation generator 202 produces an optical stimulation signal in accordance with a program based on control signals from processor 210. Optical stimulation generator 202 may also include one or more light sources 205 such as one or more lasers or one or more light-emitting diodes (LEDs) that produce optical light within optical stimulation generator 202 that is then transmitted along optical light guides 130 to provide optical stimulation treatment to a target tissue. Alternatively, light source 205 may be separate from optical stimulation generator 202 such that optical stimulation generator 202 provides the signals that power and/or control light source 205.

Electrical stimulation generator 203, under the control of processor 210, generates electrical stimulation signals for delivery to patient 112 via selected combinations of electrodes 116, 118. An example range of electrical stimulation parameters believed to be effective in DBS to manage a movement disorder of patient may include:

1. Pulse Rate, i.e., Frequency: between approximately 0.1 Hertz and approximately 500 Hertz, such as between approximately 0.1 to 10 Hertz, approximately 40 to 185 Hertz, or such as approximately 140 Hertz.
2. In the case of a voltage controlled system, Voltage Amplitude: between approximately 0.1 volts and approximately 50 volts, such as between approximately 2 volts and approximately 3 volts.

3. In the alternative case of a current controlled system, Current Amplitude: between approximately 0.2 milliamps to approximately 100 milliamps, such as between approximately 1.3 milliamps and approximately 2.0 milliamps.
4. Pulse Width: between approximately 10 microseconds and approximately 5000 microseconds, such as between approximately 100 microseconds and approximately 1000 microseconds, or between approximately 20 microseconds and approximately 450 microseconds.

Accordingly, in some examples, electrical stimulation generator 203 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves), charge balanced or the like. Stimulation signals configured to elicit ECAPs, resonant response or other evoked physiological signals may be similar or different from the above parameter value ranges.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 may control stimulation generator 202 according to therapy programs stored in memory 211 to apply particular stimulation parameter values specified by one or more of programs, such as waveform pattern, voltage amplitude or current amplitude, pulse width, or pulse rate.

In the example shown in FIG. 2, the set of electrodes 116 includes electrodes 116A, 116B, 116C, and 116D, and the set of electrodes 118 includes electrodes 118A, 118B, 118C, and 118D. Optical light guides 130 may include optical light guide 130A of lead 114A, and optical light guide 130B of lead 114B. Processor 210 may control electrical stimulation generator 203 which may include independently controllable current sources and sinks, to apply the stimulation signals to respective electrodes 116, 118. In some examples, processor 210 may control electrical stimulation generator 203 to gate transistors on at the sources or sinks as desired. In this manner, electrical stimulation generator 203 may be configured to selectively source or sink two or more electrodes to form an electrode combination for delivering electrical stimulation to the patient via the respective electrodes. Processor 210 may control one or more switches to couple or decouple sensing module 204 from electrodes 116, 118 to enable sensing from one or more electrodes and/or isolate sensing module 204 from delivered stimulation generated by electrical stimulation generator 203. Processor 210 may control optical stimulation generator 202 to apply the optical stimulation signals to respective optical light guides 130A, 130B. Processor 210 may in certain instances deliver a sub-threshold stimulation generated by electrical stimulation generator 203 that facilitates in orientation of the light guide to direct optical stimulation towards target tissue.

In other examples, IMD 106 may include a switch module (not shown) that may couple electrical stimulation signals to selected conductors within leads 114, which, in turn, deliver the stimulation signals across selected electrodes 116, 118. The switch module may be a switch array, switch matrix, multiplexer, or any other type of switching module configured to selectively couple stimulation energy to selected electrodes 116, 118 and, in some examples, to selectively sense neurological brain signals with selected electrodes 116, 118. Hence, electrical stimulation generator 203 may be coupled to electrodes 116, 118 via the switch module and conductors within leads 114. The switch module may be used for single channel or multi-channel stimulation generators.

Electrical stimulation generator 203 may be a multi-channel stimulation generator with independent current sources and sinks as described above. In particular, electrical stimulation generator 203 may be capable of delivering a single stimulation pulse, multiple stimulation pulses, or a continuous signal at a given time via a single electrode combination or multiple stimulation pulses at a given time via multiple electrode combinations. In some examples, however, electrical stimulation generator 203 may be configured to deliver multiple channels of electrical stimulation on a time-interleaved basis. For example, electrical stimulation generator 203 may comprise multiple voltage or current sources and sinks that are coupled to respective electrodes to drive the electrodes as cathodes or anodes. In this example, IMD 106 may not require the functionality of a switch module or time-interleaved multiplexing of stimulation via different electrodes.

In some examples, optical stimulation generator 202 may include multiple light sources (e.g., of different wavelengths). In some examples, optical stimulation generator 202 may include a single light source. In some examples, optical stimulation generator 202 may deliver the light via a single fiber. In some examples, optical stimulation generator 202 may deliver the light via multiple fibers (e.g., with concurrent stimulation).

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the axial locations A, B, C, and D. In some examples, light guides 130 are disposed within respective leads 114.

Although sensing module 204 may be incorporated into a common housing with optical stimulation generator 202, electrical stimulation generator 203 and processor 210 in FIG. 2, in other examples, sensing module 204 may be in a separate housing from IMD 106 and may communicate with processor 210 via wired or wireless communication techniques.

Sensor 212 may include one or more sensing elements that sense values of a respective patient parameter. For example, sensor 212 may include one or more accelerometers, optical sensors, chemical sensors, temperature sensors, pressure sensors, wearable sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient). For example, IMD 106 may determine from these one or more additional sensors the brain state (or disease/symptom state) of the patient and sense signals for determining electrode movement during a brain state of lower fluctuation or lower noise to improve signal detection. In other examples, IMD 106 may employ an inertial sensor to determine when the patient is at rest (e.g., lying down and/or sleeping) and sense signals for determining lead movement during a time of rest to reduce noise or other motion artifacts in the sensed signals. In some examples, IMD 106 may sense signals for determining lead movement in response to receiving an indication that the patient received a dose of medication or the patient has entered a physician appointment.

Telemetry module 208 supports wireless communication between IMD 106 and an external programmer 104 or another computing device under the control of processor 210. Processor 210 of IMD 106 may receive, as updates to programs, values for various stimulation parameters such as magnitude and electrode combination, from programmer 104 via telemetry module 208. The updates to the therapy programs may be stored within therapy programs portion of memory 211. In addition, processor 210 may control telemetry module 208 to transmit alerts or other information to programmer 104 that indicate a lead moved with respect to tissue. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, triggered by sensed events or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 106. In some examples, power requirements may be small enough to allow IMD 106 to utilize patient motion and implement a kinetic energy-scavenging device to trickle charge a rechargeable battery. In other examples, traditional batteries may be used for a limited period of time.

According to the techniques of the disclosure, processor 210 of IMD 106 delivers via electrodes 116, 118 interposed along leads 114, electrical stimulation therapy to and/or sense/record electrical signals from patient 112. In some examples, processor 210 of IMD delivers via optical light guides 130, optical stimulation therapy to patient 112. The DBS therapy is defined by one or more therapy programs 214 having one or more parameters stored within memory 211. For example, the one or more parameters include a waveform pattern, a current amplitude (for a current-controlled system) or a voltage amplitude (for a voltage-controlled system), a pulse rate or frequency, and a pulse width, or quantity of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time (e.g., as in cycling).

According to one or more techniques of the disclosure, processor 210 of IMD 106 may be configured to deliver electrical signals to one or more electrodes 116, 118 of leads 114 to generate a magnetic field near the electrodes 116, 118. In some examples, processor 210 of IMD 106 may be configured to deliver subthreshold electrical signals to one or more electrodes 116, 118 of leads 114 to generate a magnetic field near the electrodes 116, 118, where for example, the subthreshold electrical signals do not activate nearby tissue. In some examples, electrodes 116, 118 may include segmented electrodes and the magnetic field may be generated between two segmented electrodes at the same or different axial location. In some examples, electrodes 116, 118 may include ring electrodes and the magnetic field may be generated between a first electrode at a first axial position and a second electrode at a second axial position. In some examples, the first electrode may be a ring electrode at a first axial position and the second electrode may be a segmented electrode at a second axial position different than the first axial position.

A portion near or at a distal end of the optical light guide 130 may include metallic material such that the distal end of the optical light guide 130 may be maneuvered using the magnetic field created by the electrodes 116, 118. For example, a distal end of the optical light guide 130 may be steered due to the magnetic field acting on the metallic material to steer the distal end of the optical light guide in a desired direction. In some examples, the distal end of the optical light guide may be steered in four primary directions: anterior, posterior, medial and lateral. In some examples, the distal end of the optical light guide may be steered in four secondary directions: anterio-medial, anterio-lateral, posterior-medial and posterio-lateral. In some examples, the metallic material may include a metallic coating disposed on the distal end of the optical light guide, e.g., extending entirely or partially around the circumference of the optical light guide. In some examples, the metallic material comprises a nanofluid disposed on the distal end of the optical light guide. In some examples, the nanofluid comprises $Fe_3O_4$ (or iron oxide nanoparticles or similar). In some examples, processor 210 may select certain electrodes to steer the optical light guide 130 to a particular direction, or to multiple directions. For example, processor 210 may select a first set of electrodes to steer the distal end of optical light guide 130 in a first direction, and select a second set of electrodes to steer the distal end of optical light guide 130 in a second direction, different from the first direction. In some examples, processor 210 is steering the optical light guide 130 to target tissue. In some examples, processor 210 may select light to optically stimulate the target tissue and provide therapy.

In some examples, processor 210 may direct electrical stimulation generator 203 to provide electrical stimulation to electrodes 116, 118 after steering the optical light guide 114.

In some examples, processor 210 may direct electrical stimulation generator 203 to provide electrical stimulation to electrodes 116, 118 and may direct optical stimulation generator 202 to transmit light from the light guide 114 after steering the optical light guide 114 with the electrical stimulation generator. In some examples, processor 210 may direct optical stimulation generator 202 to transmit light from the light guide 114 after steering the optical light guide 114 with the electrical stimulation generator 203. For any of these examples, processor 210 may further direct for sensing with electrodes 116, 118. For any of these examples, processor 210 may further direct for sensing with optical sensors.

In some examples, processor 210 may automatically adjust using electrical stimulation and/or optical stimulation for delivering therapy. In some examples, processor 210 may automatically adjust parameter values for electrical stimulation and/or optical stimulation. In some examples, processor 210 may automatically steer optical light guide

130 using a magnetic field generated by the electrodes. In some examples, processor 210 may transmit an alert to programmer 104 or other external device to indicate that an updated stimulation type (optical v. electrical) may be needed to continue efficacious therapy.

FIGS. 3, 4, 5A and 5B are conceptual diagrams of example lead 314, with segmented electrodes 316A, 316B, 316C, 316D (316D not shown in FIGS. 3 and 4) carried by the lead. Lead 314 includes four segmented electrodes mounted at various circumferential (i.e., angular) positions around lead housing 380. Lead 314 is typically inserted into through cranium 122 to a target position within brain 120 (FIG. 1). Lead 314 optionally may include additional sets of segmented electrodes, e.g., a second set 416A, 416B, 416C, 416D, a third set 516A, 516B, 516C, 516D, and a fourth set 616A, 616B, 616C, 616D, at different axial levels. The additional sets of electrodes may be used for creating a magnetic field, delivering electrical stimulation and/or sensing. Although each of the additional sets of electrodes are shown as including segmented electrodes, some individual sets may be formed by a single ring electrode, rather than multiple segmented electrodes. In some examples, lead 314 may include an active/bullet tip or a passive tip lead with high or low resolution segment arrays.

Lead 314 is implanted within brain 120 at a location determined by the clinician to be near an anatomical region to be stimulated. In some examples, electrodes 316A, 316B, 316C, 316D may be equally spaced around the lead housing at different radial positions. While in FIGS. 5A, 5B only one electrode level is featured, lead 314 may include multiple levels of electrodes, as discussed above and shown in FIGS. 3 and 4. In some examples, one or more electrode levels may have one, two, three, or more segmented electrodes located at different angular positions around the circumference (e.g., around the perimeter) of lead housing 380. In some examples, one or more electrode levels may have one or more ring electrodes located at different axial positions along a longitudinal axis of lead housing 380. Electrodes of one circumferential location may be lined up on an axis parallel to the longitudinal axis of lead 314. Alternatively, electrodes of different electrode levels may be staggered around the circumference of lead housing 380. In addition, lead 314 may include asymmetrical electrode locations around the circumference, or perimeter, of each lead or electrodes of the same level that have different sizes. These electrodes may include semi-circular electrodes that may or may not be circumferentially aligned between electrode levels. Other designs resulting in a low- or high-resolution segmented lead with or without an active (bullet)/passive tip are also contemplated.

Figure 4:
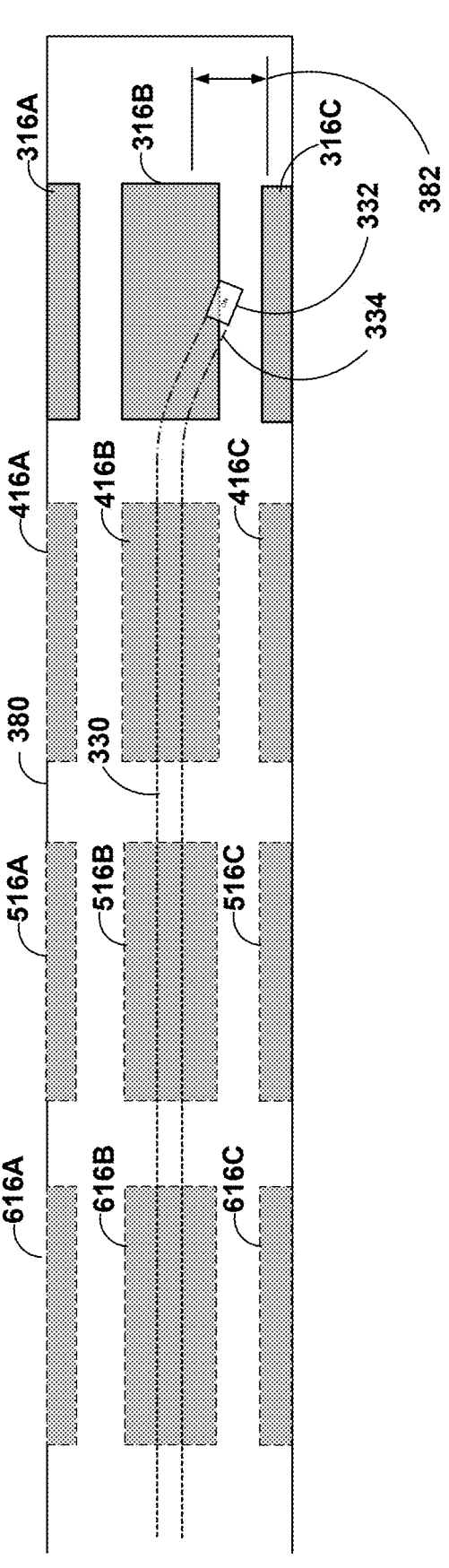
FIG. 4 is a conceptual diagram illustrating a side view of a lead of the implantable medical system in accordance with aspects of this disclosure.
Figure 5B:
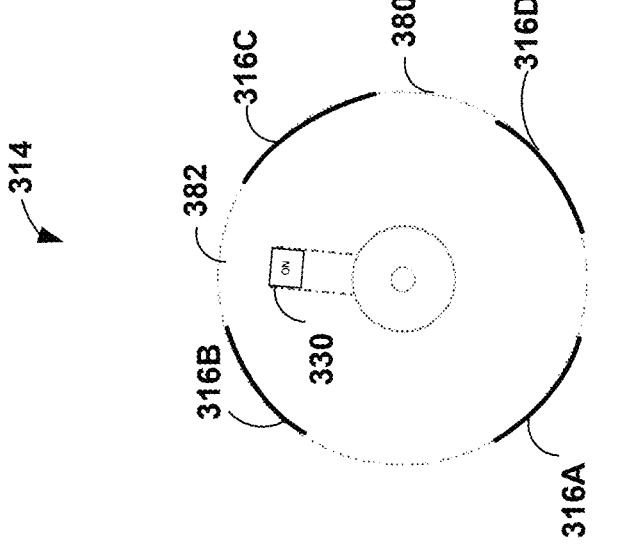
FIG. 5B is a conceptual diagram illustrating an end view of a lead of the implantable medical system in accordance with aspects of this disclosure.
Figure 5A:
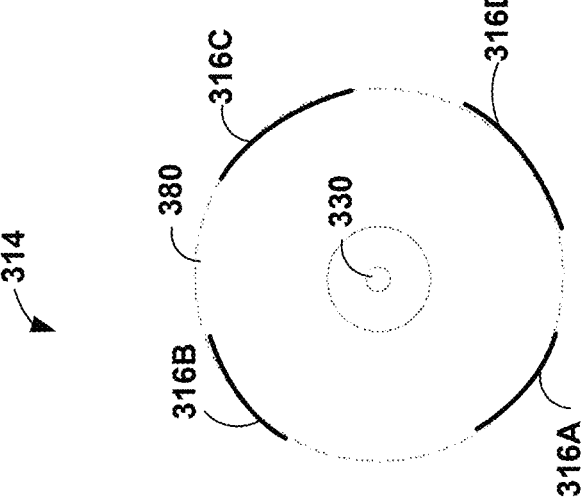
FIG. 5A is a conceptual diagram illustrating an end view of a lead of the implantable medical system in accordance with aspects of this disclosure.

In some examples, at least one optical light guide 330 is disposed within lead 314. In some examples, a distal end 334 of the optical light guide 330 may be configured to emit light from the light source 205 (FIG. 2). A portion near or at the distal end 334 of the optical light guide 330 may include metallic material 332 such that the distal end may be maneuvered using the magnetic field created by two or more of the electrodes 316A, 316B, 316D, 316D. For example, a distal end 334 of the optical light guide 330 may be steered due to the magnetic field acting on the metallic material to steer the distal end 334 of the optical light guide 330. In some examples, the metallic material may include a metallic coating disposed on the distal end of the optical light guide. In some examples, the metallic material comprises a nanofluid disposed on the distal end of the optical light guide. In some examples, the nanofluid comprises $Fe_3O_4$ (or iron oxide nanoparticles or similar). In some examples, processor 210 (FIG. 2) may select certain electrodes to steer the optical light guide 330 to a particular direction, or to multiple directions. For example, electrodes 316B, 316C may be selected to create a magnetic field to deflect the distal end 334 of optical light guide 330, as shown in FIG. 4, 5B. For example, processor 210 (FIG. 2) may direct electrical voltage across electrodes 316B, 316C to create a magnetic field in a particular location within the lead. The magnetic field may steer the distal end 334 of the optical light guide 330 to target tissue. In some examples, processor 210 may control optical stimulation generator 202 to select light to optically stimulate the target tissue and provide therapy by emitting light from light source 205 via light guide 330. In some examples, light guide 330 may emit light from a distal end of the light guide and/or through a window 382 formed near the distal end of the lead 314. Window 382 may be formed, for example, by a portion of the lead body of lead 314 that is transmissive or at least partially transmissive to wavelengths of light emitted by light guide 330. In some examples, the window may be at a distal end of the lead 314. In some examples, multiple magnetic fields generated by multiple different sets of the electrodes may steer the optical light guide 330 in multiple different directions, e.g., on a selective basis under control of electrical stimulation generator 203 and processor 210. In some examples, window 382 may be formed in between the two adjacent segments of a lead at the same level. In some examples, window 382 may be formed between a space of the electrodes (ring/segmented) at two different levels along a longitudinal axis of the lead. In some examples, window 382 may include a passive tip of the lead body.

Figure 6:
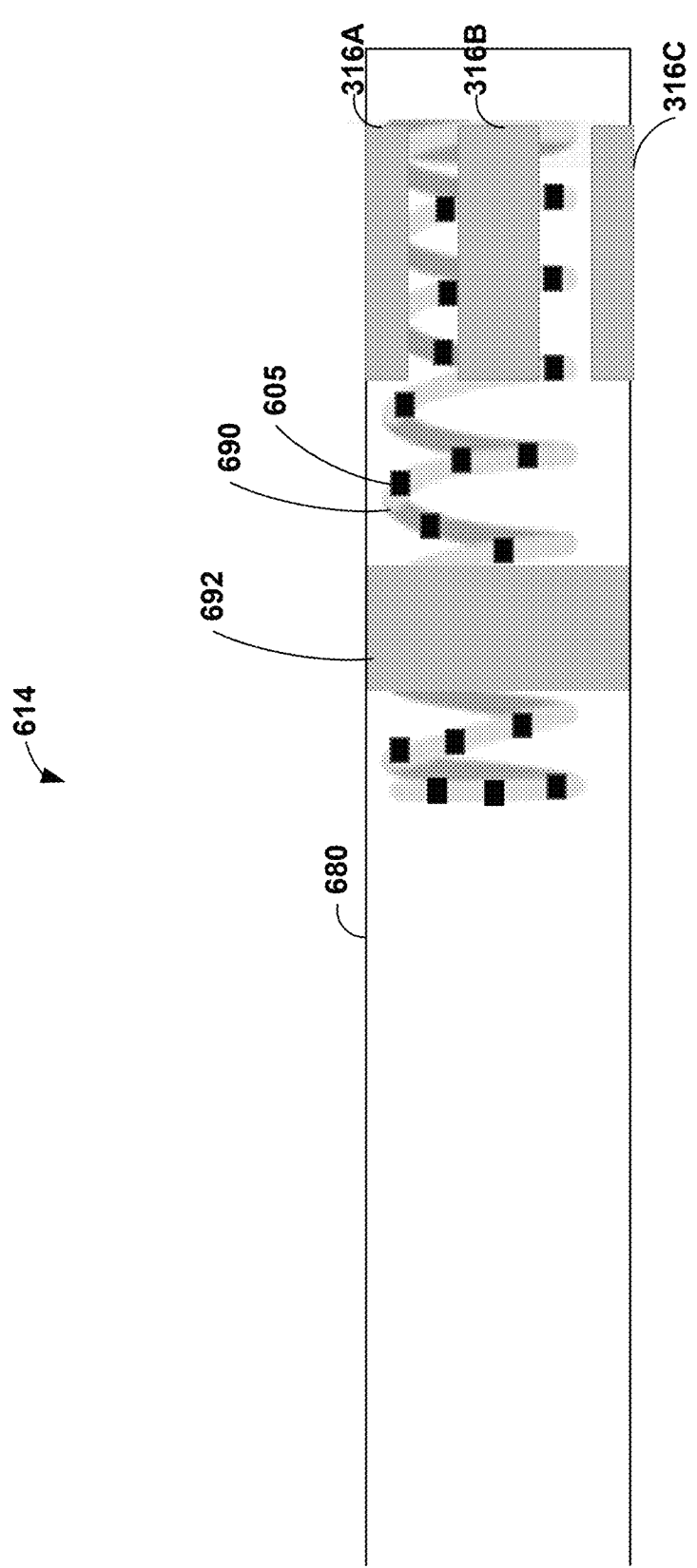
FIG. 6 is a conceptual diagram illustrating a side view of a lead of the implantable medical system in accordance with aspects of this disclosure.

FIG. 6 shows another example device, such as a lead 614 of an implantable medical system having a plurality of electrodes 316A, 316B, 316C, 316D (316D not shown) disposed along a lead body 680. As in the example of FIGS. 3, 4, 5A, and 5B, lead 614 may include multiple levels of electrodes. Lead 614 optionally may include additional sets of segmented electrodes or ring electrodes at different axial levels. The additional sets of electrodes may be used for electrical stimulation, creating a magnetic field for orienting the optic light guide and/or sensing. In some examples, lead 614 includes a ring electrode 692 at a different axial position than electrodes 316A, 316B, 316C, 316D (316D not shown).

In some examples, the plurality of electrodes 316A, 316B, 316C, 316D may be disposed near a distal end of the lead 614. In some examples, a substrate 690 may be disposed within the lead 614. The substrate 690 may have a coiled or helical shape, in some examples. In some examples, the substrate 690 may be configured to be flexible to move in a wave shape within the lead body 680.

In some examples, the substrate 690 is affected by magnetic fields, for instance including a metallic material. In some examples, substrate 690 may be formed of metallic material. In some examples, substrate 690 may be coated with metallic material. In some examples, the substate 690 may have two or more light sources 605. In some examples, light sources 605 may include LEDs (light emitting diodes). In some examples, light sources 605 may include QDs (quantum dots).

The light sources 605 may be electrically coupled with conductive traces coupled with processor 210. In some examples, processor 210 may be configured to deliver voltage across two or more of the electrodes to steer portions of the substrate 690. For example, the electrical voltage may create a magnetic field that acts on the metallic material of the substrate 690 to move the substrate, and some or all of the light sources 605 in a desired direction. In some examples, processor 210 may direct light sources to deliver light during or after the substrate 690 has been steered by the electrical voltage.

In some examples, processor 210 may be configured to deliver voltage across two or more of the electrodes and create a magnetic field to steer portions of the substrate 690. In some examples, processor 210 may be configured to deliver voltage across two or more of the electrodes to steer portions of the substrate 690 in a dynamic wave to deliver light therapy in a wave shape. In some examples, electrodes 316 may provide electrical stimulation therapy. In some examples, magnetic steering with selective activation of the light source, such as quantum dots, may result in a specific stimulation wave shape. In some examples, parameters such as wavelength, intensity, or others may be altered to achieve a desired wave shape.

Figure 7:
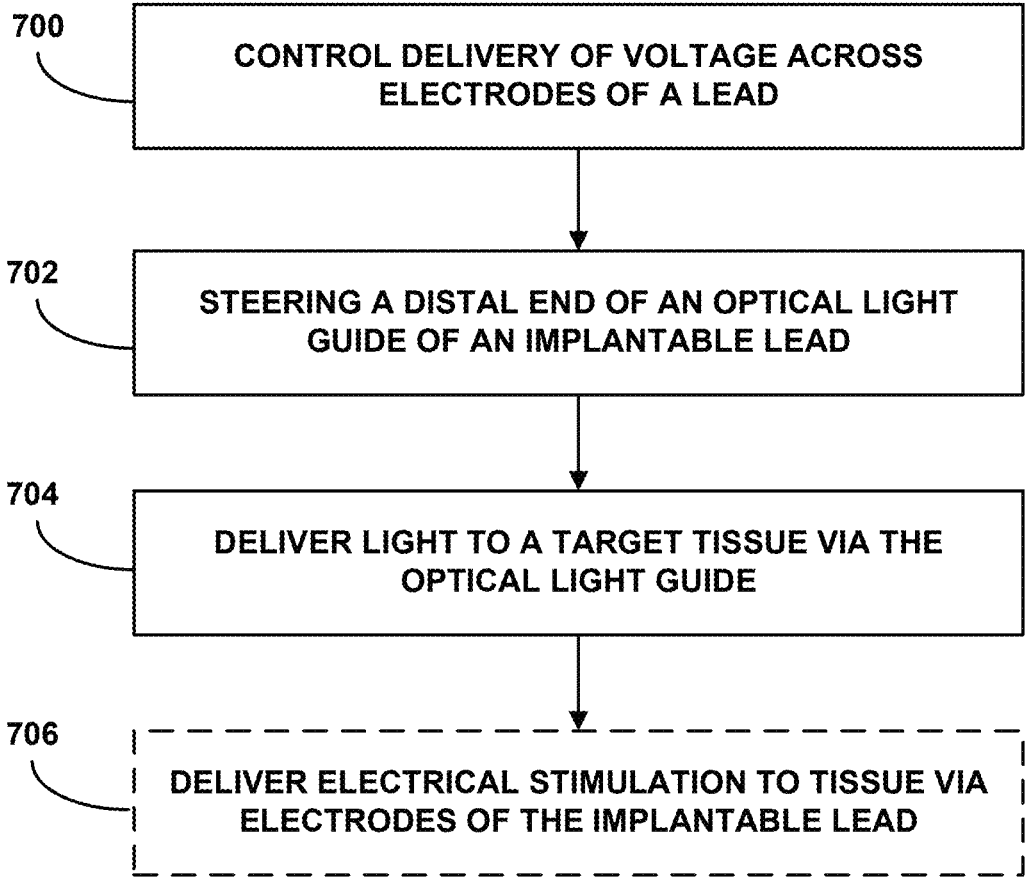
FIG. 7 is a flow diagram illustrating an example technique of the medical device system in accordance with aspects of this disclosure.

FIG. 7 is a flowchart illustrating an example technique for steering an optical light guide and providing stimulation to tissue. The technique of FIG. 7 will be described with respect to processor 210 of IMD 106 in FIG. 2. However, other processors, devices, or combinations thereof, may perform the techniques of FIG. 7 in other examples.

As shown in the example of FIG. 7, processor 210 may control delivery of voltage across electrodes of a lead (700). For example, processor 210 of IMD 106 may be configured to deliver voltage across one or more electrodes 116, 118 of leads 114 to generate a magnetic field near the electrodes 116, 118. In some examples, processor 210 of IMD 106 may be configured to deliver subthreshold voltage across one or more electrodes 116, 118 of leads 114 to generate a magnetic field near the electrodes 116, 118, where for example, the subthreshold electrical signals do not activate nearby tissue. In some examples, electrodes 116, 118 may include segmented electrodes and the magnetic field may be generated between two segmented electrodes at the same axial location. In some examples, electrodes 116, 118 may include ring electrodes and the magnetic field may be generated between a first electrode at a first axial position and a second electrode at a second axial position. In some examples, the first electrode may be a ring electrode at a first axial position and the second electrode may be a segmented electrode at a second axial position different than the first axial position.

In one or more examples, the techniques disposed herein include steering a distal end of an optical light guide (702). A portion near or at a distal end of the optical light guide 130 may include metallic material such that the distal end may be maneuvered using the magnetic field created by the electrodes 116, 118. For example, a distal end of the optical light guide 130 may be steered due to the magnetic field acting on the metallic material to steer the distal end of the optical light guide. In some examples, the metallic material may include a metallic coating disposed on the distal end of the optical light guide. In some examples, the metallic material comprises a nanofluid disposed on the distal end of the optical light guide. In some examples, the nanofluid comprises $Fe_3O_4$ (or iron oxide nanoparticles or similar). In some examples, processor 210 may select certain electrodes to steer the optical light guide 130 to a particular direction, or to multiple directions. In some examples, processor 210 is steering directional/fractionalized electrical stimulation and/or sensing patient signals from electrodes 116, 118 to target tissue.

In some examples, processor 210 may control for the optical light guide to deliver light to target tissue (704). For example, once the processor 210 has controlled delivery of electrical voltage across the electrodes of the lead and the optical light guide has been steered into a desired position toward target tissue, processor 210 may control optical stimulation generator 202 to deliver optical signals, e.g., as stimulation pulses, with intensities, wavelengths, pulse widths (if applicable), and rates specified by one or more stimulation programs. In some examples, light is guided from a light source toward tissue of a patient. In some examples, emitted light is directed through material of the lead housing, such as silicone, where the material may be transmissive or at least partially transmissive to wavelengths of light.

Processor 210 may also control optical stimulation generator 202 to selectively deliver the stimulation via subsets of optical light guides, which may be directed to different target tissue sites. Upon selection of a particular program group, processor 210 may control optical stimulation generator 202 to deliver optical stimulation according to the programs in the groups, e.g., simultaneously or on a time-interleaved basis. A group may include a single program or multiple programs. Each program may specify a set of stimulation parameters, such as stimulation pulses, intensities, wavelengths, pulse widths (if applicable), and pulse rates, if applicable. In addition, each program may specify a particular optical fiber combination for delivery of optical stimulation. The optical fiber combination may specify particular optical fibers in a single array or multiple arrays.

Optical stimulation generator 202 may include stimulation generation circuitry to generate optical stimulation pulses and circuitry for switching stimulation across different optical light guide combinations, e.g., via an optical multiplexer in response to control by processor 210. Optical stimulation generator 202 produces an optical stimulation signal in accordance with a program based on control signals from processor 210. Optical stimulation generator may also include one or more light sources 205 such as one or more lasers or one or more light-emitting diodes (LEDs) that produce optical light within stimulator that is then transmitted along optical light guides 130 to provide optical stimulation treatment to a target tissue. Alternatively, light source 205 may be separate from optical stimulation generator 202 such that optical stimulation generator 202 provides the signal that powers light source 205.

In some examples, processor 210 may optionally control electrical stimulation generator 203 to generate stimulation signals for delivery to patient 112 via selected combinations of electrodes 116, 118 (706). Hence, IMD 106 may be configured to deliver optical stimulation therapy alone or, optionally, deliver both optical stimulation and electrical stimulation, e.g., on a selective, alternating or continuous basis and/or sense/record signals. In some examples, electrical stimulation generator 203 generates electrical stimulation signals in accordance with one or more electrical stimulation parameters to provide therapy to a patient. Other ranges of therapy parameter values may also be useful, and may depend on the target stimulation site within patient 112. While stimulation pulses are described, stimulation signals may be of any form, such as continuous-time signals (e.g., sine waves), charge-balanced variants or the like. Stimulation signals configured to elicit ECAPs, resonant response or other evoked physiological signals may be similar or different from the parameter value ranges.

Example 1. An implantable medical system comprising: a light delivery module comprising a light source that generates light and a controller that controls an output of the light source; and a lead with a plurality of electrodes, the lead extending from a proximal end to a distal end, wherein the lead further comprises an optical light guide configured to deliver the light from the light source, and the controller is configured to deliver voltage across two or more of the electrodes to steer a distal end of the optical light guide.

Example 2. The implantable medical system of example 1, wherein the optical light guide comprises an optical fiber optically connected to the light source.

Example 3. The implantable medical system of any of examples 1-2, further comprising a metallic material at or near the distal end of the optical light guide, wherein the controller is configured to deliver the voltage across two or more electrodes to generate a magnetic field that acts on the metallic material to steer the distal end of the optical light guide.

Example 4. The implantable medical system of example 3, wherein the metallic material comprises a metallic coating disposed on the distal end of the optical light guide.

Example 5. The implantable medical system of example 3, wherein the metallic material comprises a nanofluid disposed on the distal end of the optical light guide.

Example 6. The implantable medical system of example 5, wherein the nanofluid comprises iron oxide nanoparticles.

Example 7. The implantable medical system of any of examples 1-6, wherein at least one of the plurality of electrodes is a segmented electrode.

Example 8. The implantable medical system of any of examples 1-7, wherein at least one of the plurality of electrodes is a ring electrode.

Example 9. The implantable medical system of any of examples 1-8, wherein the optical light guide is a single-fiber optical light guide.

Example 10. The implantable medical system of any of examples 1-8, wherein the optical light guide is a multi-fiber optical light guide.

Example 11. The implantable medical system of any of examples 1-9, wherein the light source comprises one or more light emitting diodes (LEDs).

Example 12. The implantable medical system of any of examples 1-9, wherein the light source comprises quantum dots (QDs).

Example 13. The implantable medical system of any of examples 1-12, wherein the light is selected to optically stimulate a target tissue and provide therapy.

Example 14. The implantable medical system of any of examples 1-13, further comprising electrical stimulation circuitry configured to generate electrical stimulation for delivery via one or more of the plurality of electrodes.

Example 15. The implantable medical system of any of examples 1-14, further comprising electrical sensing circuitry configured to sense electrical signals via one or more of the plurality of electrodes.

Example 16. The implantable medical system of any of examples 1-14, wherein the controller is configured to deliver voltage across two or more selected electrodes of the plurality of electrodes to selectively steer the distal end of the optical light guide in different directions.

Example 17. A system comprising: a memory; and processing circuitry configured to: control delivery of voltage across electrodes of a lead to steer a distal end of an optical light guide of the lead; and control a light source to transmit light to a patient via the optical light guide of the lead.

Example 18. A method comprising: controlling delivery of voltage across between electrodes of a lead to steer a distal end of an optical light guide of the lead; and transmitting light from a light source of an implantable medical system to a patient via the optical light guide of the lead.

Example 19. The method of example 18, wherein the optical light guide comprises a metallic material at or near the distal end of the optical light guide, wherein a controller is configured to deliver the voltage across two or more electrodes to generate a magnetic field that acts on the metallic material to steer the distal end of the optical light guide.

Example 20. The method of example 19, wherein the metallic material comprises a metallic coating disposed on the distal end of the optical light guide.

Example 21. The method of example 20, wherein the metallic material comprises a nanofluid.

Example 22. The method of example 21, wherein the nanofluid comprises iron oxide nanoparticles.

Example 23. The method of any of examples 18-22, wherein at least one of the one or more of the electrodes is a segmented electrode.

Example 24. The method of any of examples 18-23, wherein at least one of the one or more electrodes is a ring electrode.

Example 25. The method of any of examples 18-24, wherein transmitting light from the light source comprises transmitting light from one or more LEDs (light emitting diodes) or QDs (quantum dots).

Example 26. The method of any of examples 18-25, further comprising directing electrical stimulation to the patient via the one or more electrodes.

Example 27. The method of any of examples 18-26, wherein controlling delivery of voltage across electrodes of the lead to steer the distal end of the optical light guide of the lead includes steering the distal end of the optical light guide in different directions.

Example 28. An implantable medical system comprising: a lead with a plurality of electrodes along a lead body; a substrate within the lead, the substrate having two or more light sources, wherein the substrate includes metallic material; and a controller configured to deliver voltage across two or more of the electrodes to steer portions of the substrate within the lead body.

Example 29. The implantable medical system of example 28, wherein the substrate is coated in metallic material.

Example 30. The implantable medical system of any of examples 28-29, wherein the controller is configured to deliver the voltage across two or more electrodes to generate a magnetic field that acts on the substrate to steer the substrate.

Example 31. The implantable medical system of example 30, wherein the controller is configured to steer the substrate in a wave shaped movement.

Example 32. The implantable medical system of any of examples 28-31, wherein the light source comprises light emitting diodes (LEDs).

Example 33. The implantable medical system of any of examples 28-31, wherein the light source comprises quantum dots (QDs).

Example 34. The implantable medical system of any of examples 28-33, further comprising electrical stimulation circuitry configured to generate electrical stimulation for delivery via one or more of the plurality of electrodes.

Example 35. The implantable medical system of any of examples 28-34, further comprising electrical sensing circuitry configured to sense/record electrical signals via one or more of the electrodes.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a DVD, a floppy disk, a cassette, magnetic media, optical media, or other computer readable media.

Various examples have been described. These and other examples are within the scope of the following claims.

The invention claimed is:

1. An implantable medical system comprising:
   a light delivery module comprising a light source that generates light and a controller that controls an output of the light source; and
   a lead with a plurality of electrodes, the lead extending from a proximal end to a distal end,
   wherein the lead further comprises an optical light guide configured to deliver the light from the light source, wherein the optical light guide comprises a property of being affected by a magnetic field, and
   the controller is configured to deliver voltage across two or more of the electrodes to steer a distal end of the optical light guide.

2. The implantable medical system of claim 1, wherein the optical light guide comprises an optical fiber optically connected to the light source.

3. The implantable medical system of claim 1, further comprising a metallic material at or near the distal end of the optical light guide, wherein the controller is configured to deliver the voltage across two or more electrodes to generate a magnetic field that acts on the metallic material to steer the distal end of the optical light guide.

4. The implantable medical system of claim 3, wherein the metallic material comprises a metallic coating disposed on the distal end of the optical light guide.

5. The implantable medical system of claim 3, wherein the metallic material comprises a nanofluid disposed on the distal end of the optical light guide.

6. The implantable medical system of claim 5, wherein the nanofluid comprises iron oxide nanoparticles.

7. The implantable medical system of claim 6, wherein the iron oxide nanoparticles comprise Fe3O4.

8. The implantable medical system of claim 1, wherein at least one of the plurality of electrodes is a segmented electrode.

9. The implantable medical system of claim 1, wherein at least one of the plurality of electrodes is a ring electrode.

10. The implantable medical system of claim 1, wherein the optical light guide is a single-fiber optical light guide.

11. The implantable medical system of claim 1, wherein the optical light guide is a multi-fiber optical light guide.

12. The implantable medical system of claim 1, wherein the light source comprises one or more light emitting diodes (LEDs) or one or more quantum dots (QDs).

13. The implantable medical system of claim 1, wherein the light is selected to optically stimulate a target tissue and provide therapy.

14. The implantable medical system of claim 1, further comprising electrical stimulation circuitry configured to generate electrical stimulation for delivery via one or more of the plurality of electrodes.

15. The implantable medical system of claim 1, further comprising electrical sensing circuitry configured to sense electrical signals via one or more of the plurality of electrodes.

16. The implantable medical system of claim 1, wherein the controller is configured to deliver voltage across two or more selected electrodes of the plurality of electrodes to selectively steer the distal end of the optical light guide in different directions.

17. A method comprising:
controlling delivery of voltage across electrodes of a lead to steer a distal end of an optical light guide of the lead, wherein the optical light guide comprises a property of being affected by a magnetic field; and
transmitting light from a light source of an implantable medical system to a patient via the optical light guide of the lead.

18. The method of claim 17, wherein the optical light guide comprises a metallic material at or near the distal end of the optical light guide, wherein a controller is configured to deliver the voltage across two or more electrodes to generate a magnetic field that acts on the metallic material to steer the distal end of the optical light guide.

19. The method of claim 18, wherein the metallic material comprises a metallic coating disposed on the distal end of the optical light guide.

20. The method of claim 18, wherein the metallic material comprises a nanofluid.

21. The method of claim 18, wherein controlling delivery of the voltage comprises:
controlling delivery of voltage across two or more selected electrodes of the electrodes to selectively steer the distal end of the optical light guide in different directions.

* * * * *